United States Patent [19]

Jones, Jr. et al.

[11] Patent Number: 4,725,579

[45] Date of Patent: Feb. 16, 1988

[54] METHOD OF IN VITRO FERTILIZATION BY A UNIQUE COMBINATION OF GONADOTROPINS

[75] Inventors: Howard W. Jones, Jr.; Georgeanna S. Jones, both of Norfolk, Va.

[73] Assignee: Serono Laboratories, Inc., Randolph, Mass.

[21] Appl. No.: 703,997

[22] Filed: Feb. 21, 1985

[51] Int. Cl.$^4$ .................. A61K 37/38; A61B 19/00
[52] U.S. Cl. ................................. 514/12; 128/1 R
[58] Field of Search ..................... 514/12; 128/1 R

[56] References Cited

U.S. PATENT DOCUMENTS 4,589,402 5/1986 Hodgen et al. ............... 128/1 R

Primary Examiner—Delbert R. Phillips
Attorney, Agent, or Firm—Ostrolenk, Faber, Gerb & Soffen

[57] ABSTRACT

A method for the treatment of infertility is described involving recruitment of more than one oocyte by a unique and hitherto undescribed combination of goandotropins, the harvest of these oocytes prior to their spontaneous ovulation and their fertilization by exposure to sperm in vitro so that the resulting concepti can be transferred to the uteri of the donors and so overcome several forms of infertility.

8 Claims, No Drawings

METHOD OF IN VITRO FERTILIZATION BY A UNIQUE COMBINATION OF GONADOTROPINS

BACKGROUND OF THE INVENTION

Approximately 400,000 germ cells are stored in the ovaries of the human female at the time of puberty. No further germ cells are made. Beginning at the time of puberty and ending at the menopause, there are approximately 400 ovulatory menstrual cycles which consume essentially all of the germ cells in the human ovary. About 1,000 germ cells are consumed in each menstrual period. However, in any one menstrual cycle only one germ cell, developed in what becomes the dominant follicle, is ovulated and available for pregnancy.

Human reproduction is extraordinarily inefficient. In spite of normal exposure to pregnancy, the probability of a normal pregnancy is no more than 25% during any one month. Thus, three times out of four either the ovulated germ cell is not fertilized (this is very rare) or the fertilized germ cell does not implant because of abnormalities of one kind or another or if it does implant, does not develop and is aborted.

Although the details are not accurately known, the mechanism by which a single egg each month is selected to become the dominant egg is dependent upon a complex interaction between one or more secretions from the ovary and at least two pituitary glycoprotein hormones, the follicular stimulating hormone (FSH) and the luteinizing hormone (LH). While there are undoubtedly numerous intermediates, particularly products of the central nervous system, the growth of several follicles in any one cycle is under the control of the pituitary gonadotropins, particularly FSH. The final maturation process for the egg resulting in its ovulation seems to be under the control of LH.

For more than twenty years, it has been possible to induce ovulation and menstruation, and sometimes pregnancy, in patients whose ovulatory mechanism is deranged so that normal cyclic ovulation and menstruation does not occur, by the administration of suitable amounts of a 50—50 mixture of FSH and LH known as human menopausal gonadotropin (hMG).

Normally menstruating women of reproductive age are many times rendered infertile by a variety of causes which cannot be corrected by endocrinological or surgical therapy. One example of such a difficulty is related to the bilateral removal of fallopian tubes for various causes such as sequential bilateral ectopic pregnancies. Under this circumstance, it has been shown that it is possible to harvest an egg from the dominant follicle using the natural cycle, provided this egg is harvested just prior to anticipated ovulation as determined by a measurement of the levels of LH, either in the serum or in the urine. Fertilization of this egg in vitro can be achieved in approximately 80% of the patients from which an egg can be obtained. Development to the 6-8 cell stage can be achieved in some 90% of the situations where the egg has been fertilized and if transferred to the donor of the egg, pregnancy will result in less than 15% of patients so treated in the natural cycle.

It is furthermore shown that the pregnancy rate will improve if more than one egg can be matured and harvested in any one menstrual cycle. This has been accomplished by a variety of techniques including the use of human menopausal gonadotropin according to a standard regime in a normally menstruating woman. In this way, more than a single egg can be matured and harvested in a single menstrual cycle. If one mature egg is so recruited the pregnancy rate is 20%; if two mature eggs are harvested, successfully fertilized, and transferred, the probability of pregnancy increases to 27%, and if three eggs can be successfully harvested, fertilized, and transferred, the pregnancy rate will increase to 38%, an improvement almost equal to 100% of that obtained with the transfer of a single egg. Table I demonstrates that using human menopausal gonadotropin, it is seldom possible to recruit three mature eggs.

TABLE I

| PREOVULATORY EGG TRANSFERS (n = 272) | | | | |
|---|---|---|---|---|
| # Eggs | Occurrence | % | # Preg | % Preg |
| 1 | 137 | 50.4 | 28 | 20.4 |
| 2 | 99 | 36.4 | 27 | 27.3 |
| 3 | 21 | 7.7 | 8 | 38.1 |
| 4 | 10 | 3.7 | 4 | 40.0 |
| 5 | 3 | 1.1 | 0 | 0 |
| 6 | 2 | 0.7 | 1 | 50.0 |

In addition, there are some patients who are relatively refractory to hMG stimulation so that overall more than 20% of patients so stimulated fail to have a transfer of even one fertilized egg. Table II below shows that over 485 cycles, stimulation by human menopausal gonadotropin resulted in 367 transfers. Among these transfers, it was possible to recruit, fertilize and transfer two mature eggs in 131 of 367 transfers, or 38%, and it was possible to recruit, fertilize, and transfer the ideal number of three eggs only 61 of 367 times, or 16%.

TABLE II

| TRANSFERS AFTER hMG TREATMENT (n = 367) | | | | |
|---|---|---|---|---|
| # Eggs | Occurrence | % | # Preg | % Preg |
| 1 | 137 | 37.3 | 26 | 19.0 |
| 2 | 131 | 35.7 | 31 | 23.7 |
| 3 | 61 | 16.6 | 18 | 29.5 |
| 4 | 23 | 6.3 | 6 | 26.1 |
| 5 | 9 | 2.5 | 2 | 22.2 |
| 6 | 6 | 1.6 | 3 | 50.0 |

It is the object of this invention is to provide and improve the method of oocyte recruitment so that it will be possible in an increased proportion of patients to recruit eggs and in these, to recruit more mature fertilizable oocytes and thus increase the pregnancy rate over that which is possible by the recruitment of a single mature egg.

SUMMARY OF THE INVENTION

This invention relates to a method of improving the recruitment of oocytes so as to realize an improvement in the pregnancy rate after in vitro fertilization by virtue of an ability to recruit eggs from a larger pool of patients and from them to recruit multiple mature eggs greater than that possible with existing methods of oocyte recruitment. After harvesting of the eggs, they are combined with spermatozoa in vitro and subsequently transferred after fertilization into the uterus of the donor. The improvement is realized by increasing FSH administration in the early stages of hMG therapy.

DESCRIPTION OF THE INVENTION

It has been found that the use of a preparation containing a greatly increased ratio of FSH to LH early in the menstrual period greatly increases the number of patients from whom it is possible to recruit eggs and greatly increases the number of mature oocytes that it is possible to harvest in a single menstrual cycle as compared with the standard 50—50 preparation of FSH to LH currently available.

The term "early in the menstrual period" refers to the first 1 to about 4 days of the conventional hMG regimen. Preferably, the early period is the first two days. The conventional therapy is usually begun on the third day of the menstrual period. In accordance with the invention, the usual 1:1 International Units ratio of FSH to LH is increased to about 1.5:1 to 4:1, preferably about 1.75 to 2.5 and most preferably about 2:1.

One hundred twenty-six normally menstruating individuals who were infertile by virtue of a variety of disorders uncorrectable by more conventional methods were studied by inducing multiple eggs in the following manner.

Beginning on day 3 of the menstrual cycle, all patients were given 300 units of FSH and 150 units of LH by means of a standard preparation of hMG containing 150 units each of FSH and LH but in addition were given 150 additional units of FSH. The same treatment was repeated on day 4.

On day 5, 6 and subsequent days, the patients received 150 units of FSH and 150 units of LH by the standard hMG preparation. The stimulation was discontinued when the serum estradoil (E2) value has reached 300 pg/ml provided the patient exhibited a "shift" in the cervical and vaginal parameters indicating response to estrogen as described in Jones, H. W., Jr., Jones G. S., Andrews, M. C., Acosta, A. A., Bundren, C., Garcia, J. E., Sandow, B. A., Veeck, L. L., Wilkes, C., Witmyer, J., Wortham, J. W. and Wright, G. L., Jr.: The Program for In Vitro Fertilization at Norfolk. Fertil Steril. 38: 14, 1982; Garcia, J. E., Jones, G. S., Acosta, A. A. and Wright, G. L., Jr.: HMG/HCG Follicular Maturation for Oocyte Aspiration: Phase I, 1981, Fertil. Steril. 39: 194, 1983.

Under some circumstances, if the cervical and vaginal parameters had not responded as just noted, but the estradiol value reached 600 pg/ml, the stimulation was also discontinued. Following an interval of approximately 50 hours, 10,000 units of human chorionic gonadotropin (hCG) was injected as a surrogate for the spontaneous LH surge which under the stimulatory conditions has been found to occur only infrequently. Ferraretti, A. P., Garcia, J. E., Acosta, A. A. and Jones, G. S.: Serum LH During Ovulation Induction for In Vitro Fertilization in Normally Menstruating Women, Fertil. Steril. 40: 742, 1983.

Thirty-four to 36 hours after the injection of the hCG, eggs were harvested by laparoscopic technique (Jones, H. W., Acosta, A. A. and Garcia, J. E.: A Technique for the Aspiration of Oocytes from Human Ovarian Follicles, Fertil. Steril. 37: 26, 1982), were fertilized and transferred in the hope that pregnancy would occur (Jones, H. W. Jr., Acosta, A. A., Garcia, J. E., Sandow, B. A. and Veeck, L. L.: On the Transfer of Concepti From Oocytes Fertilized In Vitro, Fertil. Steril. 39: 241, 1983).

With the increase in the ratio of FSH and LH, the percentage of cycles with a transfer increased from 76% to 87%. The 126 high FSH ratio cycles were divided into patients who had been previously stimulated by hMG (and had not responded well) and previously unstimulated, i.e. new patients. Among the previously stimulated patients, the transfer rate was 85% and among the new patients, it was 89%). See Table III.

Furthermore, the number of total eggs and preovulatory eggs was increased from 3.80 to 6.14 and from 1.60 to 2.81 per cycle, respectively. The pregnancy rate per cycle of attempt was increased from 17.7 to 21.4. For previously stimulated patients, the rate was 20.7 and for new patients, 22.7.

The increase in multiple transfers may be seen by comparing Tables II and IV. With hMG alone, 27% of transfers were of 3 or more concepti while with the high FSH ratio preparation, 57.8% were of 3 or more.

In addition, the number of multiple pregnancies was increased from 11.6% to 25.9%. Giving consideration to the total number of individual pregnancies, a corrected pregnancy rate may be calculated. The corrected rate increased from 20.0% to 28.8% per cycle (Table III).

Various changes and modifications can be made in the method of this invention without departing from the spirit and scope thereof. The embodiments set forth herein were for the purpose of illustration only and were not intended to limit the invention.

TABLE III*

|  | # CYCLES | # EGGS | % TR | TOTAL EGGS PER CY | PREOV EGGS PER CY | # PREG | # TWINS | # TRIPLETS | % PREG PER CY | % MULTIPLE PREG | CORRECTED PREG RATE CY |
|---|---|---|---|---|---|---|---|---|---|---|---|
| HMG | 485 | 367 | 76 | 3.80 | 1.60 | 86 | 10 | 0 | 17.7 | 11.6 | 20.0 |
| FSH/HMG | 126 | 109 | 87 | 6.14 | 2.81 | 27 | 5 | 2 | 21.4 | 25.9 | 28.8 |
| FSH/HMG (previous HMG therapy) | 82 | 70 | 85 | 5.62 | 2.56 | 17 | 3 | 2 | 20.7 | 29.4 | 29.3 |
| FSH/HMG (no previous HMG therapy) | 44 | 39 | 89 | 7.11 | 3.30 | 10 | 2 | 0 | 22.7 | 20.0 | 27.3 |

*TR = transfers;
CY = cycle;
PREG = pregnancy;
PREOV = preovulatory

TABLE IV

| # Eggs | Occurrence | % | # Preg | % Preg |
|---|---|---|---|---|
| 1 | 18 | 16.5 | 2 | 11.1 |
| 2 | 28 | 25.7 | 5 | 17.9 |
| 3 | 18 | 16.5 | 5 | 27.8 |
| 4 | 16 | 14.7 | 5 | 31.3 |
| 5 | 11 | 10.1 | 3 | 27.3 |
| 6 | 18 | 16.5 | 7 | 38.9 |

What is claimed is:

1. In the method of recruiting oocytes for in vitro fertilization by administering exogenous human menopausal gonadotropin containing a 1:1 I.U. ratio of FSH to LH, the improvement which comprises administering additional FSH in an amount sufficient to establish a ratio of about 1.5:1 to 4:1 total I.U. FSH to LH per day for the first 1 to about 4 days of human menopausal gonadotropin therapy.

2. The method of claim 1, wherein said FSH to LH ratio during said 1 to about 4 days is about 1.75:1 to 2.5:1.

3. The method of claim 2, wherein said FSH to LH ratio during said 1 to about 4 days is about 2:1.

4. The method of claim 3, wherein said additional FSH is administered for the first two days of therapy.

5. The method of claim 4, wherein said therapy is initiated on the third day of the menstrual cycle.

6. The method of claim 5, wherein said additional FSH administered per day is 150 I.U.

7. The method of claim 6, wherein the recruited oocytes are harvested and fertilized in vitro.

8. The method of claim 1, wherein the recruited oocytes are harvested and fertilized in vitro.

* * * * *